(12) United States Patent
Duong et al.

(10) Patent No.: US 10,092,671 B2
(45) Date of Patent: Oct. 9, 2018

(54) DEVICE FOR DISPERSING FOUL GASEOUS EFFLUENT EMISSIONS AT THE SOURCE

(71) Applicant: SUEZ GROUPE, Paris la Defense (FR)

(72) Inventors: Frederic Duong, Pezilla-la-Riviere (FR); Robert Kelly, La Celle Saint Cloud (FR); Patrick Chantre, Portiragnes (FR)

(73) Assignee: SUEZ GROUPE, Paris la Defense (FR)

( * ) Notice: Subject to any disclaimer, the term of this patent is extended or adjusted under 35 U.S.C. 154(b) by 240 days.

(21) Appl. No.: 15/118,007

(22) PCT Filed: Feb. 12, 2015

(86) PCT No.: PCT/IB2015/051052
§ 371 (c)(1),
(2) Date: Aug. 10, 2016

(87) PCT Pub. No.: WO2015/121820
PCT Pub. Date: Aug. 20, 2015

(65) Prior Publication Data
US 2017/0007735 A1    Jan. 12, 2017

(30) Foreign Application Priority Data
Feb. 14, 2014   (FR) ...................... 14 51164

(51) Int. Cl.
*A61L 9/00*     (2006.01)
*G01D 11/26*    (2006.01)
(Continued)

(52) U.S. Cl.
CPC ............ *A61L 9/14* (2013.01); *B01F 3/04056* (2013.01); *B01F 5/04* (2013.01); *B05B 12/18* (2018.02);
(Continued)

(58) Field of Classification Search
CPC ... A61L 9/015; A61L 9/00; A61L 9/14; F23G 7/06; F23J 15/00; F23L 17/16
(Continued)

(56) References Cited

U.S. PATENT DOCUMENTS 2,544,769 A * 3/1951 Sperry ................... C23G 3/00
454/66

FOREIGN PATENT DOCUMENTS

| EP | 0 772 003 A1 | 5/1997 |
| EP | 2 161 446 A1 | 3/2010 |
| WO | 2010/044055 A1 | 4/2010 |

OTHER PUBLICATIONS

International Search Report, dated Jun. 17, 2015, from corresponding PCT Application.

* cited by examiner

*Primary Examiner* — Monzer R Chorbaji
(74) *Attorney, Agent, or Firm* — Young & Thompson

(57) ABSTRACT

A device for dispersing foul gaseous effluent emissions released diffusely by sources located close to the ground, in particular by wastewater treatment ponds (10, 11, 12), includes: at least two auxiliary air or gas injectors (5*a*1, 5*b*1; 5*a*2, 5*b*2; 5*a*3, 5*b*3) oriented upwards and installed in opposing zones on the periphery of each foul gaseous effluent source, such as to disperse the gaseous effluents; separate supply elements (8.1, 13*a*1, 13*b*1; 8.2, 13*a*2, 13*b*2; 8.3, 13*a*3, 13*b*3) for the injectors; and wind-direction-sensitive control elements for ensuring that at least the injector(s) best located to disperse and/or lift the gaseous effluent plume are supplied.

15 Claims, 2 Drawing Sheets

Figure 1:
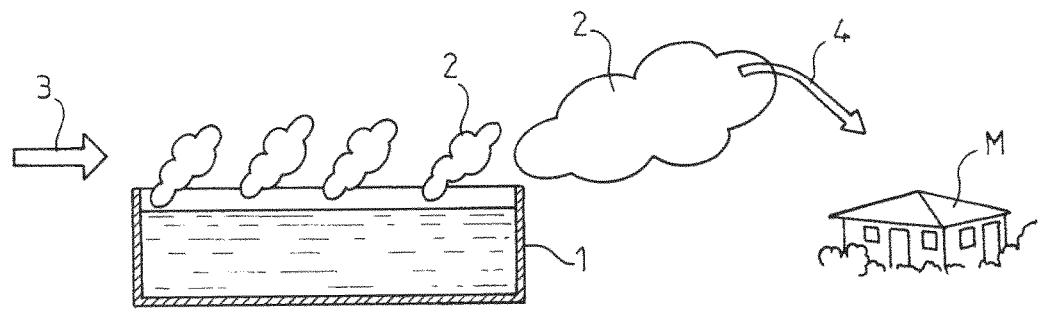

(51) Int. Cl.
*F23L 17/02* (2006.01)
*B65B 1/30* (2006.01)
*A61L 9/14* (2006.01)
*B01F 3/04* (2006.01)
*B01F 5/04* (2006.01)
*F23L 17/16* (2006.01)
*B05B 12/18* (2018.01)

(52) U.S. Cl.
CPC ............... *F23L 17/16* (2013.01); *A61L 9/00* (2013.01); *A61L 2209/111* (2013.01); *A61L 2209/21* (2013.01); *B01F 2215/009* (2013.01); *B08B 2215/003* (2013.01); *F23J 2215/00* (2013.01); *F23L 2700/001* (2013.01)

(58) Field of Classification Search
USPC ........ 422/4, 105, 119, 900; 141/192; 454/15
See application file for complete search history.

DEVICE FOR DISPERSING FOUL GASEOUS EFFLUENT EMISSIONS AT THE SOURCE

The invention relates to a device for dispersing, at the source, foul gaseous effluent emissions that are released diffusely by sources located close to the ground, in particular by wastewater treatment tanks or any other activity that releases odors.

Many industrial activities emit foul odors that are dispersed by the wind. These smells cause considerable discomfort for residents. Odor emissions are difficult to control, in particular when it is not possible to confine them in a leaktight chamber, and when the emission areas are large and have variable geometry.

The odors experienced relate to the concentration and to the chemical nature of the molecules produced at the source of odors. Numerous meteorological factors influence the emissions and above all the dispersion of the odors in the environment. These are in particular:
  the speed and direction of the wind,
  the humidity and temperature of the ambient air,
  the atmospheric pressure,
  the effect of the relief and of the neighboring buildings that may produce downdrafts.

Various means for reducing the impact of olfactory nuisances have been proposed.

Case of Channeled Flows

In order to promote the dispersion of the foul air or gases, after a chemical or biological treatment, the gaseous effluents may be dispersed at a certain height into the atmosphere by stacks. The height of the stacks varies depending on the nature and the composition of the gases, the regulations in force and the results of the dispersion study of the gaseous, particulate and malodorous pollutants.

The dispersion of gases into the environment is improved by increasing the stack height. A regime of turbulent and sustained winds has the effect of mixing the gases with the ambient air and thus promoting the dispersion of the pollutants.

The pollutant-dispersing effect that is linked to the height for ejecting the gases into the atmosphere is sometimes destroyed by downdrafts (downward winds). These unfavorable conditions may lead to a concentration of pollutants or odors at the ground that is greater than the maximum allowable threshold experienced, despite meeting the regulations regarding releases of pollutants leaving the outlets.

WO 2010/044 055 proposed to improve and promote the dispersion of gases by providing at least one auxiliary gas or air injector installed close to the outlet of a stack and directed upward so as to disperse the gases.

Case of Diffuse Flows

The emissions may be diffuse and originate, for example, from large tanks of treatment plants, landfill centers, organic waste storage zones, organic matter maturation areas, and other similar facilities. Such facilities are not necessarily open-air facilities, and may be at least partly covered, but the gaseous effluents are no longer channeled to an outlet, in particular a stack. It is then no longer possible or difficult and expensive to capture the foul smells at the source, and one means used to combat the odors consists in masking these odors by diffusing "white" products, the objective of which is to reduce the olfactory impact, by covering the odors.

Such a means has a very limited effectiveness since it only acts locally in the diffusion zone of the masking products. Furthermore, the molecules used are not completely environmentally neutral.

Measurement of the Odor Units

In order to objectively evaluate the ambient odor level, electrochemical sensors have been developed. Such sensors are positioned in areas with a human presence in order to continuously measure the concentration of the most odorous molecules such as $H_2S$, $NH_3$, mercaptan. These sensors make it possible to convert the chemical measurements into odor units that refer to human odor perception, and indicate the current nuisance factor.

These sensors are useful since they make it possible to warn residents of an emission peak and to warn the public before an a posteriori observation which leads to many complaints. However, these odor measurements have no corrective effect on the emissions or on the perception thereof.

The objective of the invention is, above all, to provide a device that makes it possible to significantly improve the dispersion of the foul gaseous effluents released diffusely by facilities that do not make it possible to channel these effluents.

According to the invention, the device for dispersing, at the source, foul gaseous effluent emissions, released diffusely by sources located close to the ground, in particular by wastewater treatment tanks, is characterized in that it comprises:
  at least two auxiliary gas or air injectors directed upward, installed at the periphery of one, or of each, foul gaseous effluent source, in opposite zones, so as to disperse the foul gaseous effluents,
  separate means for supplying the injectors,
  and control means sensitive to the wind direction in order to ensure the injector(s) best located for dispersing and/or raising the gaseous effluent plume is (are) supplied.

Preferably, the device according to the invention is a device for dispersing foul gaseous effluent emissions at the source, characterized in that it comprises:
  a foul gaseous effluent source tank,
  at least two auxiliary gas or air injectors ($5a$, $5b$) directed upward, installed at the periphery of the foul gaseous effluent source tank, in opposite zones, so as to disperse the foul gaseous effluents,
  means for supplying the injectors, each injector being supplied by a separate supply means,
  and control means sensitive to the wind direction arranged in order to select the start-up of the injector(s) best located, depending on the wind direction, for dispersing and/or raising the gaseous effluent plume.

Preferably, the device comprises odor detectors distributed at the periphery of a facility comprising at least one source of foul odors, these detectors being arranged in order to communicate the results of their measurements to a central measurement acquisition station connected to a control unit which, depending on the results of the measurements, actuates at least one fan in order to supply at least one appropriate section of injectors.

Generally, the injectors are located at a height lower than that of the upper edge of the source of odors, in particular alongside the odor emission zone, that is to say close to the upper edge of the source of odors.

Advantageously, the device comprises at least three sections of injectors installed at the periphery of one, or of each, foul odor source, each section comprising at least one injector.

Each angular section, and its injectors, are supplied by an air manifold equipped with a motorized control valve, the manifold being connected to the discharge of a fan.

Preferably, the injectors have an adjustable orientation.

The means for supplying the injectors and the control means may be provided to ensure a pressure that varies as a function of the atmospheric conditions and of odor unit measurements.

Advantageously, the control unit is driven by management and control software programmed to take into consideration the dispersion parameters and the odor unit measurements in real time.

The control unit may be driven by simulation software that predicts the natural dispersion of the odor plume, which is integrated for a preventive action of automatically controlling the dispersion device by induction.

The device may comprise a means for injecting "masking" products into the air that supplies the injectors.

Advantageously, the means for supplying the injectors comprise at least one adjustable-speed fan, and at least one connection pipe between the outlet of the fan and a manifold of the injector(s).

Preferably, the means for supplying the injector(s) are adjustable in order to make it possible to regulate the pressure and the flow rate of auxiliary gas or air sent to the injectors depending on the atmospheric conditions of the moment, and the properties of the gas plume, the supply means being shut down when the natural dispersion is sufficient or the conditions for which the emissions of odors are low.

Figure 2:
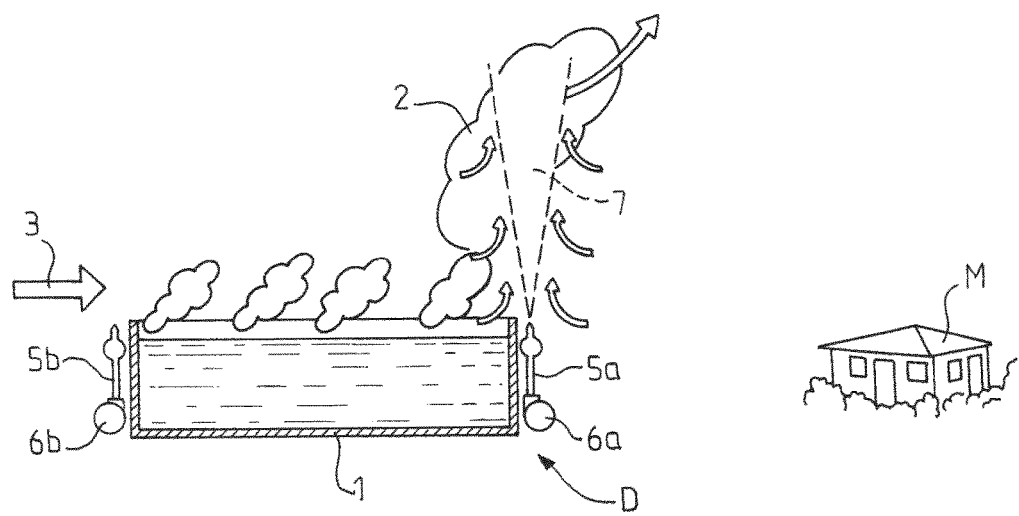
Figure 3:
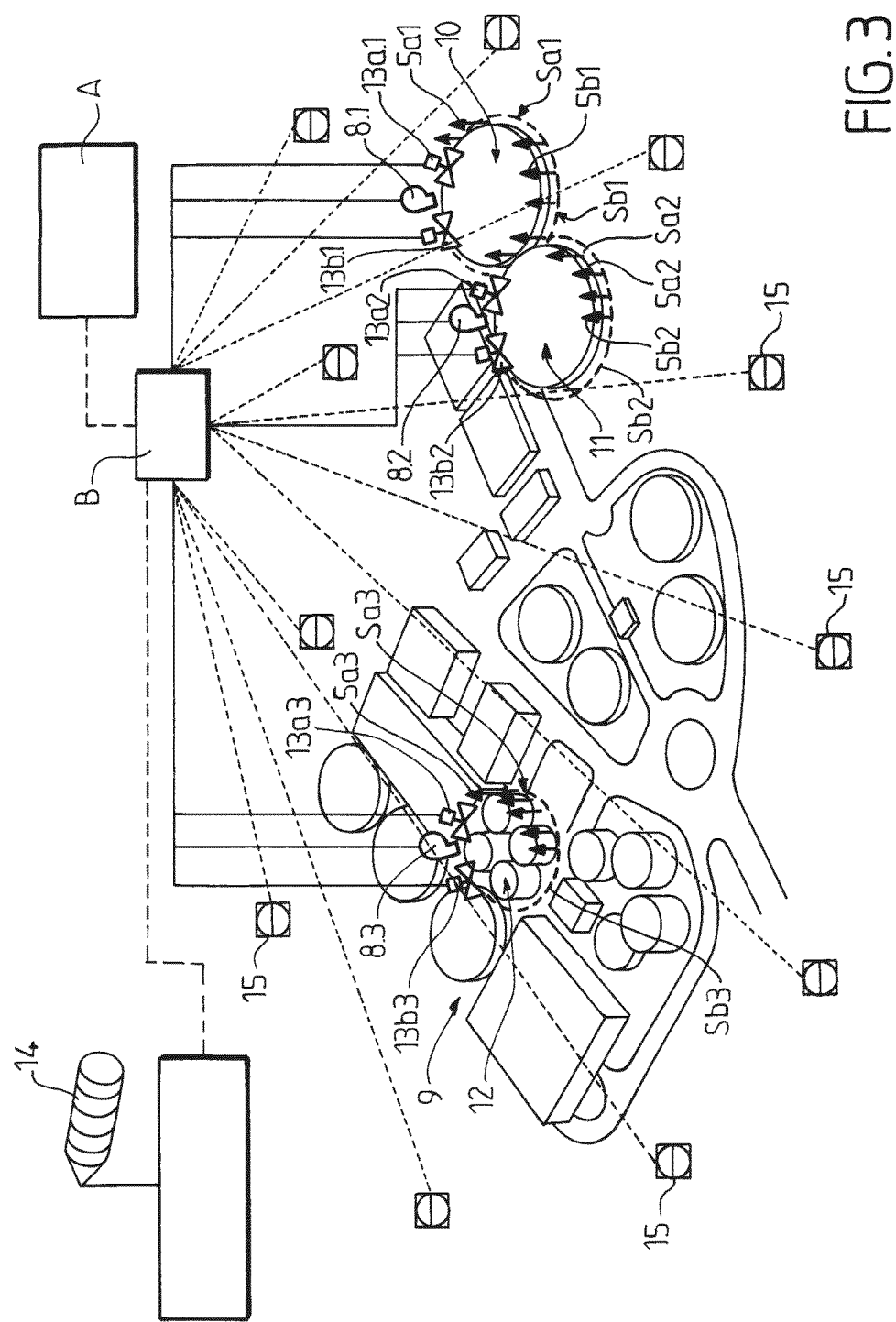

The invention consists, apart from the arrangements set out above, of a certain number of other arrangements that will be mentioned more explicitly hereinbelow with respect to examples described with reference to the appended drawings, but which are in no way limiting. In these drawings:

FIG. 1 is a diagram illustrating a water treatment tank according to the prior art, FIG. 2 is a diagram, similar to that of FIG. 1, of the tank with a device according to the invention for dispersing the gaseous effluent emissions, and FIG. 3 is a diagram of a wastewater treatment plant, the various foul gaseous effluent sources of which are equipped with devices according to the invention.

With reference to FIG. 1 of the drawings, a wastewater treatment tank 1, according to the prior art, can be seen. Such a tank is generally circular, and its diameter may reach 30 m and more. The tank 1 releases plumes 2 of foul gaseous effluents.

The volume of the plumes 2 depends essentially on the evaporation and therefore on parameters consisting of the speed of the air sweeping the surface of the tank, the ambient temperature, the hygrometry and the atmospheric pressure. The plumes 2 are driven by the wind, the direction of which is depicted by an arrow 3 and may reach dwellings M, which are on the side of the tank facing the direction of the wind. Their inhabitants will thus be inconvenienced by the effluents released. This discomfort will be even greater in the case of downward winds, illustrated by the arrow 4 in FIG. 1, in the direction of the dwellings.

In order to increase the dispersion of the foul odors into the ambient air, a device D (FIG. 2) according to the invention comprises at least two auxiliary gas or air injectors 5a, 5b directed upward and forming inductors for dispersing the gaseous effluents. The injectors 5a, 5b are supplied with medium-pressure air, especially between 50 daPa and 300 daPa, by manifolds 6a, 6b connected to the discharge of a fan not seen in FIG. 2. The supply pipes or manifolds, such as 6a, 6b, are advantageously made of spiral-seam sheet metal or made of other light (especially textile) material.

The injectors 5a, 5b are placed at the periphery of each odor emission source, so as to ensure a rapid dispersion of the odors by the dilution thereof in the ambient air. The injectors 5a, 5b are located close to the ground, at a height near the emission zone. The induction created by an air jet 7 directed upward favors the dynamic rising and the dispersion of the malodorous plume 2 when the effects of a downward wind are greater than those due to the difference in density between the gases and the ambient air.

The manifolds 6a, 6b form separate means for supplying the injectors. Thus, each injector 5a, 5b is supplied by a separate supply means.

The distribution of drive air to the injectors 5a, 5b may thus be divided so as to make it possible to select the injector(s) to be started up depending on the direction of the wind and the emission location of the odors. According to the diagram from FIG. 2, it is sufficient to operate the injector 5a located on the side of the tank 1 facing the direction of the wind 3, in order to obtain a satisfactory effect.

Advantageously, as illustrated in FIG. 3, control means B sensitive to the wind direction and to various meteorological parameters, are provided in order to ensure the injector(s) best located for dispersing and raising the gaseous effluent plume is (are) supplied.

Thus, the control means B sensitive to the wind direction are arranged in order to select the start-up of the injector(s) 5a, 5b best located, depending on the wind direction, for dispersing and/or raising the gaseous effluent plume.

The pressure at the outlet of the air jets is variable and can be adjusted so as to continuously adapt the degree of induction, or degree of entrainment of the plume by the jet 7 directed upward, relative to the requirements and in order to limit the consumption of energy, essentially electrical energy, of the device for supplying drive air. This supply device comprises, for each source of odors, at least one medium-pressure, especially from 50 daPa to 300 daPa, variable-speed, adjustable fan 8.1, 8.2, 8.3 (FIG. 3).

FIG. 3 shows a wastewater treatment plant 9, equipped with devices according to the invention with several injectors 5a1 . . . 5b3 installed at the periphery of odor emission zones consisting of tanks 10, 11, and of a zone 12 of treatment tanks, or of surface areas for storing waste and maturing organic or other matter. At each source of malodorous smells, the injectors 5a1, . . . 5b3 are distributed over at least two sections Sa1, Sb1 . . . Sa3, Sb3 around the source. Each section is supplied independently with pressurized air by a manifold, the flow rate of which is controlled by a damper or a motorized valve 13a1 . . . 13b3, located on either side of an injection of air originating from a fan 8.1, 8.2, 8.3.

For the tank 10, two sections Sa1, Sb1 of injectors 5a1, 5b1 are provided around the tank. Each section extends substantially following a semicircle and is supplied respectively, by means of a damper or of an automated valve 13a1, 13b1, by a fan 8.1, the discharge of which is connected to a portion of pipe between the valves 13a1 and 13b1 controlling the flow rate to the sections Sa1, Sb1.

The injectors 5a1, 5b1, represented in a reduced number in order to simplify FIG. 3, are preferably regularly distributed at the periphery of the source of odors formed by the tank 10. The distance between two neighboring injectors may be of the order of at least 1 m, and may reach 5 m and more depending on the perimeter to be treated. The wind direction detected by a windsock 14 and the strength of the wind detected by an anemometer (not represented) are transmitted to a central measurement acquisition station B, and the supply of pressurized air is sent to the section located on the side of the tank facing the wind direction.

Similar arrangements are adopted for the tank 11 and for the emission source 12, identical elements being denoted by the same references assigned 2 or 3 as the last number.

The number of sections of injectors positioned at the periphery of a source may be greater than two in order to better take into account the direction of the wind and to limit the number of injectors per section. Advantageously, each section of injectors is supplied separately.

The air jets 7 directed upward make it possible to break up the stream of foul gases and to rapidly disperse the odor plume during periods of downward winds.

The adjustment of the air pressure is carried out by a speed regulator of the motor of the fan 8.1, 8.2, 8.3 in question, or by any other mechanical means, especially a damper.

The air pressure at the injectors is adjusted by the central station B, generally between 50 daPa and 300 daPa, depending on the atmospheric conditions, direction and intensity of the wind, external temperature and pressure. The injectors may be completely shut down when the meteorological conditions are favorable to the natural dispersion of the odors, especially by high wind, or on the contrary by complete calm with high atmospheric pressure.

Odor sensors 15, especially electrochemical ones, are distributed at an appropriate distance all around the plant 9 in order to carry out a continuous measurement of the concentration of the most malodorous molecules such as $H_2S$, $NH_3$, mercaptan. The results of the measurements thus carried out are transmitted to the central station B for acquiring the various meteorological measurements and parameters. The data collected by the central station B is transmitted to a unit A consisting of a computer equipped with a program for management and automatic control of the various functions. A digital display, not represented, makes it possible to indicate the displacement of the odor plume, the measurements and the dispersion equipment in action. The central station B controls the actuators of the valves 13a1, 13b1 . . . 13b3 in order to adjust their operation, especially with regard to the flow rate.

The positioning of the odor sensors 15 around the plant 9 makes it possible to act in real time and to adjust the operation of the device for dispersing the malodorous effluents by induction, taking into account the meteorological conditions of the site: wind speed and direction, air temperature and humidity, atmospheric pressure. The measurements provided by the sensors 15 make it possible to correct the operating parameters and to verify the effectiveness of the device.

The operation of the device for combating the emissions of malodorous gaseous effluents results from the foregoing explanations.

If the information provided by the odor sensors 15 does not reveal an odor level that exceeds a given threshold, the central station B keeps the fans 8.1, 8.2, 8.3 shut down and the valves 13a1, 13b1 . . . 13a3, 13b3 in the closed position.

If the sensors 15 signal that the given threshold has been exceeded in a zone, generally located on the side of the plant facing the wind direction, the central station B orders the switching-on of at least one of the fans 8.1, 8.2, 8.3, and the opening of the appropriate valve 13a1 . . . 13b3, so that the appropriate injectors are started up.

The sensors 15 make it possible to verify whether the dispersion efficiency is sufficient for the odor level to drop below the given threshold.

Should the odor level not be able to be brought down to a value below the tolerable threshold, an operator will warn the plant staff and the residents, or will shut down, insofar as possible, the sources of malodorous gaseous effluents.

The device with air injectors according to the invention makes it possible to provide two effects: a dilution of the malodorous gaseous effluent plume and an effect of raising this plume.

Masking products may be injected simultaneously into the air that supplies the injectors 5a1 . . . 5b3.

Software for modelling the dispersion of the various sources of malodorous gaseous effluents is advantageously installed in the unit A to make it possible to anticipate the intensity of formation of malodorous gaseous effluents, and the formation of plumes depending on the meteorological conditions. It is then possible to act preventively by operating the appropriate sections of injectors.

The device according to the invention relates not only to open-air facilities, but also facilities of semi-closed type, that is to say those that comprise a cover with outlet orifices without high stacks. These are in particular treatment plant sludge-drying greenhouses; such greenhouses comprise a roof in which openings are provided for discharging the effluents. According to the invention, air injectors could be distributed around a greenhouse in order to disperse the effluents that escape through the roof openings.

The invention has many advantages.

The automatic controlling of the device for dispersing odors by induction, controlled by the control system comprising the odor sensors 15, makes it possible to control and manage the level of odor units at the periphery of the plant 9, and also to continuously optimize the operation of the device both preventively and by corrective action depending on the various parameters measured.

The energy consumption of the device is relatively low compared to the sizeable dilution effect with the ambient air. The device is regulated automatically in order to obtain the maximum dispersion effect while limiting its electrical energy consumption.

The device is simple to use and inexpensive with regard to a facility for the capture and chemical/biological treatment of malodorous gaseous effluents. The device can be installed on new or existing units.

The invention applies to any facility to be protected from diffuse olfactory pollution, especially
  WWTP (wastewater treatment plant) thickening or aeration tanks,
  waste storage stations,
  platforms for composting organic matter,
  waste transfer stations,
  any open industrial activity zone that emits foul odors.

The invention claimed is:

1. A device for dispersing foul gaseous effluent emissions at the source, comprising:
   a foul gaseous effluent source tank,
   at least two auxiliary gas or air injectors directed upward, installed at the periphery of the foul gaseous effluent source tank, in opposite zones, so as to disperse the foul gaseous effluents,
   means for supplying the injectors, each injector being supplied by a separate supply means,
   and control means sensitive to the wind direction arranged in order to select the start-up of the injector(s) best located, depending on the wind direction, for dispersing and/or raising the gaseous effluent plume.

2. The device as claimed in claim 1, further comprising odor detectors distributed at the periphery of a plant comprising at least one source of foul odors, these detectors being arranged in order to communicate the results of their measurements to a central measurement acquisition station (B) connected to a control unit (A) which, depending on the results of the measurements, actuates at least one fan in order to supply at least one appropriate section of injectors.

3. The device as claimed in claim 2, wherein each appropriate section of injectors is supplied by an air manifold equipped with a motorized control valve, the manifold being connected to the discharge of a fan.

4. The device as claimed in claim 2, wherein the control unit (A) is driven by management and control software programmed to take into consideration the dispersion parameters and the odor unit measurements in real time.

5. The device as claimed in claim 4, wherein the control unit (A) is driven by simulation software that predicts the natural dispersion of the odor plume, which is integrated for a preventive action of automatically controlling the dispersion device by induction.

6. The device as claimed in claim 2, wherein the control unit (A) is driven by simulation software that predicts the natural dispersion of the odor plume, which is integrated for a preventive action of automatically controlling the dispersion device by induction.

7. The device as claimed in claim 2, wherein the injectors are located close to the upper edge of the source of odors.

8. The device as claimed in claim 2, further comprising at least three sections of injectors installed at the periphery of one, or of each, foul odor source, each section comprising at least one injector.

9. The device as claimed in claim 1, wherein the injectors are located close to the upper edge of the source of odors.

10. The device as claimed in claim 1, further comprising at least three sections of injectors installed at the periphery of one, or of each, foul odor source, each section comprising at least one injector.

11. The device as claimed in claim 1, wherein the injectors have an adjustable orientation.

12. The device as claimed in claim 1, wherein the means for supplying the injectors and the control means are provided to ensure a pressure that varies as a function of the atmospheric conditions and of odor unit measurements.

13. The device as claimed in claim 1, further comprising a means for injecting "masking" products into the air that supplies the injectors.

14. The device as claimed in claim 1, wherein the means for supplying the injectors comprise at least one adjustable-speed fan, and at least one connection pipe between the outlet of the fan and a manifold of the injector(s).

15. The device as claimed in claim 14, wherein the means for supplying the injector(s) are adjustable in order to make it possible to regulate the pressure and the flow rate of auxiliary gas or air sent to the injectors depending on the atmospheric conditions of the moment, and the properties of the gas plume, the supply means being shut down when the natural dispersion is sufficient.

* * * * *